(12) United States Patent
Wulfman et al.

(10) Patent No.: US 6,475,225 B1
(45) Date of Patent: Nov. 5, 2002

(54) ABLATION ASSEMBLY WITH ELASTOMERIC DRIVESHAFT CONNECTION

(75) Inventors: Edward I. Wulfman, Woodinville; Natalya Peskin, Redmond, both of WA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/846,055

(22) Filed: Apr. 30, 2001

(51) Int. Cl.[7] .............................................. A61B 17/00
(52) U.S. Cl. ..................................................... 606/159
(58) Field of Search ........................... 606/1, 159, 170, 606/171, 180, 167, 174; 604/22

(56) References Cited

U.S. PATENT DOCUMENTS 6,022,363 A * 2/2000 Walker et al. ............... 606/159
6,077,282 A * 6/2000 Shturman et al. ........... 606/159

* cited by examiner

*Primary Examiner*—Kevin T. Truong
(74) *Attorney, Agent, or Firm*—Christensen O'Connor Johnson Kindness PLLC

(57) ABSTRACT

An ablation assembly (10) is disclosed having a drive assembly (16) positioned in a housing (29) and movable along a longitudinal path of motion within the housing. A tubular shaft (30) extends along a longitudinal axis of the housing between the drive assembly and the end of the housing. The drive assembly includes a turbine (22) coupled to an elastomeric plug (19). An aperture (20) extends longitudinally through the elastomeric plug. A tube (15) is attached to a proximal end of a driveshaft (12) and an ablation instrument (11) is coupled to the distal end of the driveshaft. The tube has a sufficient length to be inserted through the tubular shaft until the proximal end of the tube engages the elastomeric plug with an interference fit within the aperture, thereby coupling the driveshaft to the drive assembly.

7 Claims, 3 Drawing Sheets

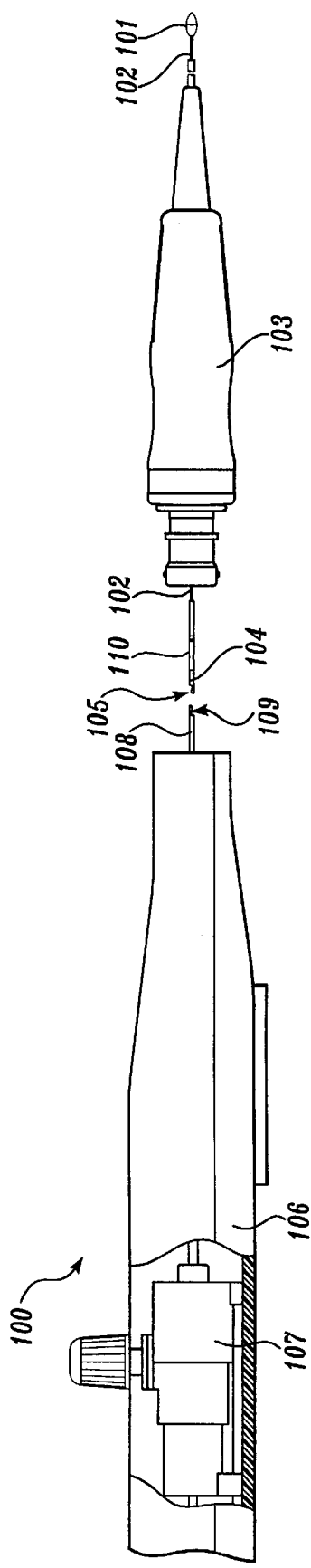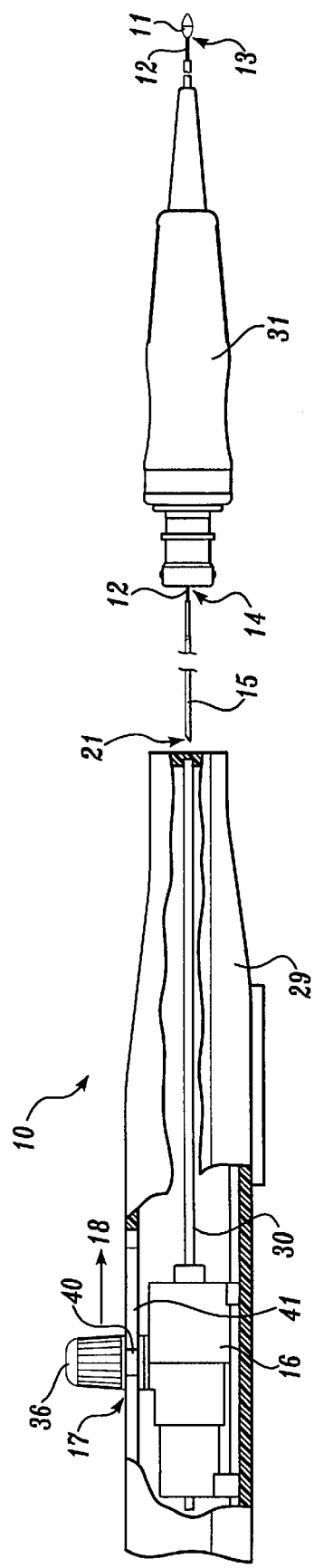
Fig. 1. (PRIOR ART)
Fig. 2.

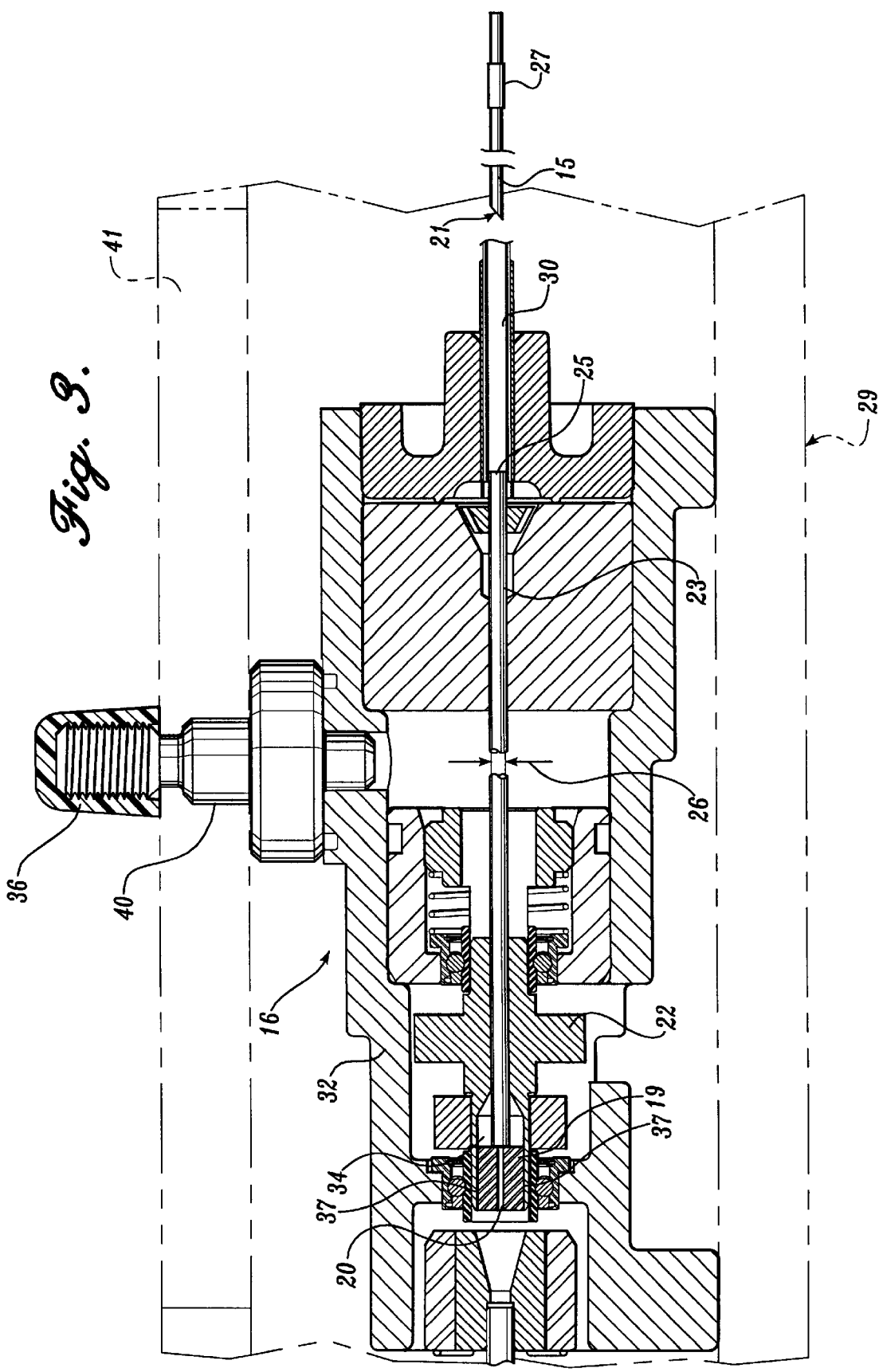

ABLATION ASSEMBLY WITH ELASTOMERIC DRIVESHAFT CONNECTION

FIELD OF THE INVENTION

This invention relates to a method and apparatus for ablating unwanted material from a patient's vasculature, and more particularly, to rotational ablation atherectomy devices.

BACKGROUND OF THE INVENTION

Vascular diseases, such as atherosclerosis and the like, have become quite prevalent in the modern day. These diseases may manifest themselves in a number of ways, often requiring different forms or methods of treatment for curing or mitigating the adverse effects of the diseases. For example, vascular diseases may take the form of deposits or growths in a patient's vasculature which restrict, in the case of a partial occlusion, or, stop, in the case of a total occlusion, blood flow to a certain portion of the patient's body. This can be particularly serious if, for example, such an occlusion occurs in a portion of the vasculature that supplies vital organs with blood or other necessary fluids.

To treat these diseases, a number of different therapies have been developed. For example, medical instruments have been developed that remove the material occluding a vascular lumen. Such instruments, sometimes referred to as atherectomy devices, use a variety of material removal instruments, such as rotating cutters or ablative burrs, for example, to remove the occluding material. (The term "atherectomy device" as used in the specification refers to a device for removing an occlusion in any portion of a patient's vasculature. Thus, while the atherectomy devices provided in accordance with preferred embodiments of the present invention are well suited for use in the coronary arteries, their use is not limited to the coronary arteries.) In rotational atherectomy devices, the material removal instrument is typically rotated via a flexible driveshaft that is connected to an electric motor or a turbine.

In operation, a guide wire is first routed from a point on the patient's exterior to the site of the occlusion. The material removal instrument is then advanced over the guide wire until it is positioned just proximal to the occlusion. The motor or turbine then rotates the driveshaft and the material removal instrument. As the material removal instrument is rotating, it is advanced through the occluded vessel. The material removal instrument removes the occluding material from the vessel, rather than merely displacing or reforming the material as is done in a balloon angioplasty procedure.

One example of a rotational ablation atherectomy device is the Rotablator® system, sold by Boston Scientific Corporation. This system includes an advancer housing that encloses an air-driven turbine drive assembly. A material removal instrument comprising an ablation burr coupled to a flexible driveshaft, is rotatably connected to the drive assembly. Depending on the location of the occlusion within a patient's vasculature and other considerations, a burr of a particular shape and/or size is selected, and the driveshaft length is specified. The driveshaft is coupled to the drive assembly in the advancer housing, such that torque from the drive assembly is transmitted through the driveshaft to the burr. The burr is advanced and retracted through the occlusion via longitudinal motion of the drive assembly.

In current embodiments of the Rotablator® system, the driveshaft is coupled to the drive assembly, by a thin connector tube that is attached to a proximal end of the driveshaft. The connector tube must be axially aligned with and connected to a second thin connector tube extending distally from the drive assembly. The connector tubes are interlocked and held in place with a tubular sheath that slides over the interlocked joint. Such a connection is sometimes referred to as a "handshake" connection. The driveshaft and drive assembly tubes are narrow, having a diameter of approximately 1 millimeter. It may be difficult therefore to align and interlock the connector tubes even under optimal conditions. When performing an atherectomy procedure, however, the cardiologist or other operator of the device wears surgical attire and a stiff shield to protect against x-rays, making it more difficult for the operator to perform the precise movements needed to couple a conventional handshake connection.

Given the considerations discussed above, it is desirable to provide a rotational ablation atherectomy device in which it is easier to couple the drive assembly to the driveshaft. The present invention fulfills this need, and provides further related advantages.

SUMMARY OF THE INVENTION

Briefly, the present invention provides an improved ablation assembly that is easier to use. In a preferred embodiment, a drive assembly is positioned within a housing, and is slidably movable along a longitudinal axis of the housing. A hollow shaft is coupled to a prime mover in the drive assembly, such as an electric motor or turbine, and extends towards a distal end of the housing. An elastomeric plug is positioned in the drive assembly, and a longitudinal aperture extends through the elastomeric plug in axial alignment with the shaft. An ablation instrument, such as a rotatable burr, is coupled to a distal end of a flexible driveshaft. A connector tube is coupled to a proximal end of the driveshaft, the tube being adapted to connect the driveshaft to the drive assembly.

In order to assist the operator in grasping and manipulating the driveshaft and associated connector tube, a catheter-body connector slidably engages the driveshaft adjacent the proximal end, such that the driveshaft extends longitudinally through the catheter. The connector tube is inserted into the drive assembly shaft until a proximal end of the connector tube is pushed into the aperture of the elastomeric plug. An interference fit is created between the connector tube and the elastomeric plug, thereby coupling the driveshaft to the drive assembly.

Although the elastomeric plug may be positioned in various locations in the drive assembly, in a preferred embodiment, it is provided in an aperture extending axially from the prime mover. In order to facilitate insertion of the connector tube into the shaft, a proximal end of the tube is tapered or formed as a smooth ball on the end of the tube. Also, in a preferred embodiment, a stop is provided on the connector tube that abuts a distal end of the shaft when the connector tube is engaged by the elastomeric plug.

In this manner, the driveshaft is easily coupled to the drive assembly by simply pushing the proximal end of the connector tube into the shaft extending through the housing. The connector tube coupled to the proximal end of the driveshaft extends through the length of the shaft and into the elastomeric plug. If it is desired to remove the ablation instrument from the advancer housing, the catheter-body connector is disconnected and the tube is pulled away from the housing, thereby disengaging the driveshaft tube from the elastomeric plug.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 1 is a side elevational view of a prior art ablation assembly;

FIG. 2 is a partially cut away, side view of an ablation assembly in accordance with an embodiment of the present invention;

FIG. 3 is a cross-sectional view of shwing the drive assembly and related components of the ablation assembly illustrated in FIG. 2.

DETAILED DESCRIPTION OF THE PREFERRED EMBODIMENT

Figure 4A:
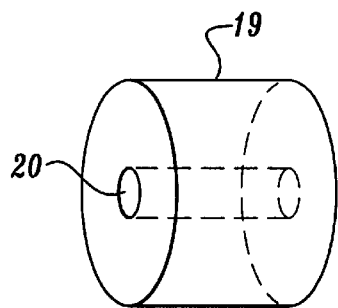
FIGS. 4A–4E are perspective views of alternative embodiments of the elastomeric plug for the ablation assembly shown in FIG. 2, showing alternative longitudinal aperture configurations.

A prior art ablation assembly 100 is illustrated in FIG. 1. An ablation instrument 101, such as a rotatable burr, is coupled to a distal end of a flexible driveshaft 102. A catheter-body connector 103 is positioned near the proximal end of the driveshaft 102, to increase the operator's ease of grasping and manipulating the driveshaft 102. A drive assembly 107 is positioned within an advancer housing 106. The drive assembly contains a turbine (not shown), and is movable along a longitudinal path of motion.

In order to operate the ablation assembly 100, it is necessary to couple the driveshaft 102 to the drive assembly 107. In a currently available system, sold by Boston Scientific Corporation and illustrated in FIG. 1, a tube 104 is coupled to a proximal end of the driveshaft 102. Similarly, a second tube 108 extends distally from an end region of the advancer housing 106. In order to couple the driveshaft 102 to the drive assembly 107, a proximal end 105 of tube 104 has a cutaway section that mates with a correspondingly shaped cutaway section at the distal end 109 of second tube 108. The tubes 104 and 108 are very fine, having a diameter on the order of 1 millimeter. Given the small size of the tubes, relatively precise manipulations are needed in order to align and interlock the mating sections of the tubes 104 and 108. To secure the tube 104 to the second tube 108, a sheath 110 is slid over the joined ends of the interlocked tubes 104 and 108.

The second tube 108 is attached to a second driveshaft (not shown) that extends into the drive assembly 107, such that torque is transmitted from the drive assembly 107 to the driveshaft 102 through the connection of tubes 104 and 108. Also, longitudinal movement of the ablation instrument 101 is achieved by moving the drive assembly 107 forward along its longitudinal path of motion in the housing 106.

An ablation assembly 10 provided in accordance with one embodiment of the present invention is illustrated in FIGS. 2 and 3. In the disclosed embodiment, an ablation instrument 11, such as a rotatable burr, is coupled to a distal end 13 of rotatable driveshaft 12. A tube 15 is coupled to a proximal end 14 of driveshaft 12. To further increase the ease with which the tube 15 and driveshaft 12 may be grasped and manipulated, a catheter-body connector 31 surrounds the driveshaft 12, adjacent the proximal end 14 of the driveshaft 12. In the preferred embodiment, the tube has a tapered proximal end 21.

A rotational advancer mechanism comprising a drive assembly 16 is positioned within an advancer housing 29. The drive assembly 16 is movable from a first retracted position 17, forward along a longitudinal path of motion 18. Although this may be done in a variety of ways, in a preferred embodiment, a knob 36 is coupled to the drive assembly 16 through a threaded shaft 40 that extends through a slot 41 in the housing 29. The drive assembly 16 is released for lateral movement by unscrewing the knob 36. Moving the knob 36 forward and backward along the slot 41 will then cause the drive assembly 16 to slide forward and backward. A pumpshaft 23 extends longitudinally through the drive assembly 16, as seen in FIG. 3. A shaft tubular 30 is axially aligned with the pumpshaft 23 and is fixed to a distal end of the drive assembly 16. The tubular shaft 30 extends towards a distal end of the housing 29.

As best seen in FIG. 3, the drive assembly 16 includes a compressed-air driven turbine 22 positioned in a turbine housing 32. In order to operate the ablation assembly, it is necessary to couple the driveshaft 12 to the drive assembly 16, such that torque from the turbine 22 is transmitted to the driveshaft 12 causing it to rotate, and longitudinal movement of the drive assembly 16 will selectively advance and retract the ablation instrument 11.

An elastomeric plug 19 is provided in the drive assembly 16. Although a variety of materials may be used, in a preferred embodiment, the elastomeric plug 19 is made from rubber or a thermoplastic elastomer such as that sold under the brand name Krayton™. Although the elastomeric plug 19 may be coupled to the drive assembly 16 in various positions, in a preferred embodiment, it is positioned adjacent turbine 22 in an aperture 34 defined by flanges 37 extending from the turbine 22 such that the plug 19 is secured within and rotates with the turbine 22.

In the embodiment shown in FIG. 3, a cylindrical aperture 20 extends longitudinally through the elastomeric plug 19. Tube 15 is secured to the proximal end of the driveshaft 12, and the proximal end 21 of tube 15 is inserted through the tubular shaft 30. To couple the driveshaft 12 to the turbine 22, the tube 15 is inserted completely through the tubular shaft 30 and the pumpshaft 23 until the proximal end 21 engages the aperture 20 of elastomeric plug 19. The aperture 20 is sized to create an interference fit between the tube 15 and the elastomeric plug 19. The interference fit between the tube 15 and elastomeric plug 19 couples the driveshaft 12 to the drive assembly 16, such that the ablation instrument 11 is advanced with forward motion of the drive assembly 16, and further, the ablation instrument 11 is rotatably coupled with the turbine 22.

Figure 4B:
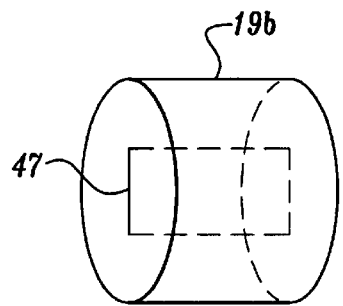
Figure 4C:
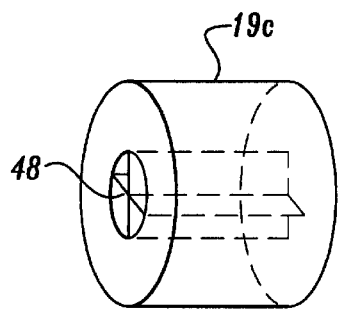
Figure 4D:
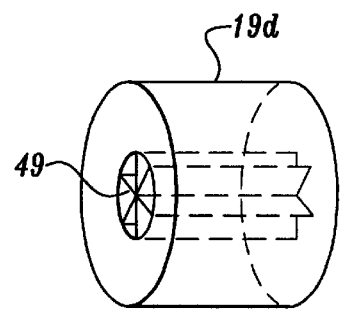
Figure 4E:
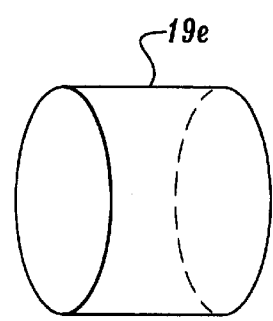

Although the ablation assembly embodiment shown in FIG. 3 has an elastomeric plug 19 with cylindrical aperture 20, other aperture shapes are also contemplated by the present invention. For example, FIGS. 4A–4E show four possible plug configurations. These aperture shapes are intended as a representative selection of contemplated aperture shapes and not as an exhaustive or limiting disclosure. FIG. 4A shows the circular aperture 20 also shown in FIG. 3. FIG. 4B discloses a single slot 47 in a plug 19b, FIG. 4C shows an alternative aperture comprising two crossed slots 48 that extend through a plug 19c, and FIG. 4D shows yet another alternative comprising three slots 49 that cross at a single line, and extend through a plug 19d. FIG. 4E shows an elastomeric plug 19e with no pre-cut central aperture, wherein an aperture would be created when the ablation assembly 10 is assembled, by the insertion of the tube 15 through the plug 19e.

Referring again to FIG. 3, the pumpshaft 23 has an inner diameter 26 of sufficient width to accommodate the tube 15.

In order to facilitate the insertion of the tube 15 into the pumpshaft 23, the proximal end 21 is tapered. Alternatively, the proximal end 21 of tube 15 may have a rounded profile. The catheter-body connector 31 (FIG. 2) surrounds the driveshaft 12 adjacent its proximal end 14, such that the driveshaft 12 extends longitudinally through the center of the catheter-body connector 31. To further ensure correct placement of the tube 15, a stop 27 is coupled to the tube 15 at an axial location such that the stop 27 abuts the distal end 25 of the pumpshaft 23 when the proximal end 21 of tube 15 is properly engaged by the elastomeric plug 19. To ensure a secure coupling, the elastomeric plug 19 and associated aperture 20 preferably have a length of about 0.5 inches.

Therefore, the driveshaft 12 is easily coupled to the drive assembly 16 by inserting the tapered proximal end 21 of the tube 15 into the shaft 30 and through the pumpshaft 23 until the proximal end 21 is secured in the elastomeric plug 19. If it is desired to remove or replace the ablation instrument 11, the operator simply disconnects the catheter-body connector 31 and pulls the tube 15 away from the housing 29, thereby disengaging the tube 15 from the elastomeric plug 19.

For safety considerations, it is desirable that the strength of the friction connection between the tube 15 and elastomeric plug 19 be less than the strength of the connection between the ablation instrument 11 and driveshaft 12. Thus, if the ablation instrument 11 becomes lodged and unable to rotate, the connection between the tube 15 and elastomeric plug 19 should fail before the connection between the ablation instrument 11 and driveshaft 12 fails. More particularly, the turbine 22 will continue to spin, but the tube 15 will slip within the elastomeric plug 19. The driveshaft 12 will therefore simply cease to spin, rather than shearing off the ablation instrument 11.

From the foregoing, it will be appreciated that although embodiments of the invention have been described herein for purposes of illustration, various modifications may be made without deviating from the spirit of the invention. For example, although the invention has been described for use with a rotational ablation instrument, it will be apparent that the invention is equally applicable for use with other material removal instruments, such as rotating cutters. Thus, the present invention is not limited to the embodiments described herein, but rather is defined by the claims which follow and equivalents thereof.

The embodiments of the invention in which an exclusive property or privilege is claimed are defined as follows:

1. An ablation assembly comprising:

a driveshaft having a proximal end and a distal end;

a material removal instrument coupled to the distal end of the driveshaft;

a tube having a proximal end and a distal end, wherein the distal end is coupled to the proximal end of the driveshaft;

a rotational drive assembly movable from a first position forward along a path of motion; and an elastomeric plug coupled to the rotational drive assembly for rotation therewith, wherein the proximal end of the tube is insertable into the elastomeric plug to create an interference fit with the elastomeric plug thereby coupling the driveshaft to the rotational drive assembly;

wherein the interference fit created between the elastomeric plug and the tube has a strength that is less than the strength by which the material removal instrument is coupled to the distal end of the driveshaft.

2. The ablation assembly of claim 1 wherein the elastomeric plug includes an aperture extending longitudinally therethrough into which the proximal end of the tube is inserted.

3. The ablation assembly of claim 1, wherein the drive assembly comprises a turbine positioned in a housing and the elastomeric plug is coupled to the turbine.

4. The ablation assembly of claim 2 further comprising a housing enclosing the rotational drive assembly, the housing including a tubular shaft aligned with an axis of rotation of the rotational drive assembly wherein the tube extends through the tubular shaft when the tube engages the elastomeric plug.

5. The ablation assembly of claim 4 wherein said tube further comprises a stop that abuts a distal end of the pumpshaft when the proximal end of the tube is fitted within the elastomeric plug.

6. The ablation assembly according to claim 1, wherein the proximal end of the tube is tapered.

7. The ablation assembly of claim 1, wherein the proximal end of the tube is rounded.

* * * * *